United States Patent
Sotome et al.

(10) Patent No.: US 7,163,965 B2
(45) Date of Patent: Jan. 16, 2007

(54) PROCESS FOR PRODUCING POROUS COMPOSITE MATERIALS

(75) Inventors: Shinichi Sotome, Tokyo (JP); Toshimasa Uemura, Ibaraki (JP); Junzo Tanaka, Ibaraki (JP); Masanori Kikuchi, Ibaraki (JP); Kenichi Shinomiya, Tokyo (JP); Soichiro Itoh, Tokyo (JP); Tetsuya Tateishi, Ibaraki (JP)

(73) Assignees: Japan Science and Technology Agency, Saitama (JP); National Institute for Materials Science, Ibaraki (JP); National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 10/492,300

(22) PCT Filed: May 1, 2002

(86) PCT No.: PCT/JP02/04355

§ 371 (c)(1),
(2), (4) Date: Apr. 12, 2004

(87) PCT Pub. No.: WO03/092759

PCT Pub. Date: Nov. 13, 2003

(65) Prior Publication Data

US 2005/0004242 A1    Jan. 6, 2005

(51) Int. Cl.
*A61L 27/00* (2006.01)
*A61L 27/52* (2006.01)

(52) U.S. Cl. .......................... 521/64; 521/61; 521/92; 521/102; 623/11.11; 623/16.11; 623/23.51; 623/23.61; 434/423

(58) Field of Classification Search ................. 521/64, 521/92, 102, 61; 623/11.11, 16.11, 23.51, 623/23.61; 424/423
See application file for complete search history.

(56) References Cited

U.S. PATENT DOCUMENTS 5,776,193 A * 7/1998 Kwan et al. ................. 424/423

FOREIGN PATENT DOCUMENTS

| JP | 07-101708 | 4/1995 |
| JP | 11-199209 | 7/1999 |
| JP | 2000-005298 | 1/2000 |
| WO | WO97/14376 | 4/1997 |

* cited by examiner

*Primary Examiner*—Irina S. Zemel
(74) *Attorney, Agent, or Firm*—Westerman, Hattori, Daniels & Adrian, LLP.

(57) ABSTRACT

This invention relates to a process for producing porous and composite materials comprising steps of: freezing a complex containing at least one calcium salt selected from calcium carbonate, calcium phosphate, and hydroxyapatite and collagen, at least a part of which is gelatinized; and then lyophilizing the resultant. The porous and composite materials obtained by the method of the present invention have large pore diameters, high porosities, and adequate mechanical strengths and biodegradability. Thus, they are suitable for implants such as bone fillers, drug carriers for sustained-release, and the like.

12 Claims, 12 Drawing Sheets
(12 of 12 Drawing Sheet(s) Filed in Color)

A

B 1 mm

A: 45°C 30min       B: 45°C 90min

A

B 1 mm

A: 25%GA 2μl        B: 25%GA 5μl

A: −20℃      B: −80℃

PROCESS FOR PRODUCING POROUS COMPOSITE MATERIALS

TECHNICAL FIELD

The present invention relates to a process for producing porous and composite materials. More particularly, the present invention relates to a process for producing porous and composite materials having large pore diameters, high porosities, and mechanical strengths that are suitable for implants such as bone fillers.

BACKGROUND ART

In the past, bone defects used to be restored by a technique of transplanting a part of a subject's own bones or a technique of complementing or replacing bones with artificial implants. Such alternative bone implants were required to have properties such as bioadaptability or bone conductivity and bone inductivity (a property of incorporating bone tissue and accelerating bone formation) in addition to mechanical properties similar to those of biological bones. Accordingly, porous materials such as porous ceramics used to be preferably employed as alternative bone implants because they were easily penetrated by bone tissues and they had good bone conductivity and bone inductivity.

Currently commercialized porous hydroxyapatite, however, is nonabsorbable. Even though this hydroxyapatite was porous, cells could not penetrate pores that did not communicate with the exterior because of this nonabsorbability. Accordingly, the final strength was not very high. Also, it was likely to collapse upon moisture absorption during surgical operations. Thus, the use thereof in surgical operation, which required strength, was difficult.

Bone fillers of porous $\beta$-TCP, which is bioabsorbable and has porosity of 75%, are commercialized (Osferion®, Olympus Optical Co., Ltd.; average pore diameters: 100 μm to 400 μm). This $\beta$-TCP is highly likely to collapse when it is handled. Thus, it was difficult to prepare this material in a form that is adequate for the transplant site, and was difficult to handle since implants easily become detached from the transplant site.

Under the above circumstances, the present inventors have conducted various studies to develop a composite material of hydroxyapatite and collagen that has a structure similar to that of biological bones and to improve its properties. For example, JP Patent Publication (Kokai) No. 7-101708 A (1995) discloses a process for producing a complex of apatite and an organic substance having the Young's modulus similar to that of biological bones with the gradual addition of a mixed solution of collagen and phosphoric acid in a suspension of calcium hydroxide. JP Patent Publication (Kokai) No. 11-199209 A (1999) discloses that a structure similar to that of biological bones can be realized by regulating pH and temperature at the time of reaction. Further, JP Patent Publication (Kokai) No. 2000-5298 A discloses a technique for enhancing the formation of apatite on a collagen surface with the use of organic acid.

In spite of these efforts, however, many complexes of hydroxyapatite and collagen that were obtained by the conventional technique had small pore diameters (approximately 0 μm to 100 μm) and had low porosities (50% or lower).

An object of the present invention is to provide novel porous and composite materials having large pore diameters, high porosities, and mechanical strengths that are suitable for implants such as bone fillers.

The present inventors have conducted concentrated studies in order to attain the above object. As a result, they have found that composite materials having large pore diameters and high porosities could be obtained by gelatinizing a part of the collagen constituting a complex of hydroxyapatite and collagen, followed by freezing and lyophilization thereof. They have also found that application of surface crosslinking to the composite material realized mechanical strengths that were suitable for implants such as bone fillers. This has led to the completion of the present invention.

More specifically, the present invention provides the following (1) to (12).

(1) A process for producing porous and composite materials comprising steps of: cooling a complex containing at least one calcium salt selected from calcium carbonate, calcium phosphate, and hydroxyapatite and collagen, at least a part of which is gelatinized, to gelate the gelatin; freezing it; and then lyophilizing the resultant.

(2) A process for producing porous and composite materials comprising a step of introducing surface crosslinking between collagens to the porous and composite materials obtained by the process according to (1) above.

(3) The process according to (2) above, wherein the step of introducing surface crosslinking is carried out by immersing the porous and composite materials in a solution containing a crosslinking agent.

(4) The process according to any one of (1) to (3) above comprising a step of adding a crosslinking agent to gelatinized collagen to introduce internal crosslinking between collagens.

(5) The process according to any one of (1) to (4) above, wherein the calcium salt is hydroxyapatite.

(6) A process for producing porous and composite materials comprising the following steps of:
  1) gelatinizing at least a part of the collagen constituting a complex containing hydroxyapatite and collagen;
  2) introducing internal crosslinking between collagens with the addition of a crosslinking agent to the complex;
  3) obtaining porous and composite materials by cooling the complex to gelate the gelatin, freezing it, and then lyophilizing the resultant; and
  4) introducing surface crosslinking between collagens by immersing the porous and composite materials in a solution containing a crosslinking agent.

(7) The process according to any one of (2) to (6) above, wherein internal and/or surface crosslinking between collagens is introduced using glutaraldehyde as a crosslinking agent.

(8) The process according to any one of (2) to (7) above, wherein surface crosslinking between collagens is introduced by immersing the porous and composite materials in a solution containing a crosslinking agent comprising ethanol as a solvent.

(9) The process according to any one of (1) to (8) above, wherein the resulting porous and composite materials have porosities of 80% or higher.

(10) The method according to any one of (1) to (9) above using a complex comprising the c-axis of hydroxyapatite being oriented along collagen fibers.

(11) Porous and composite materials having porosities of 80% or higher, which are produced by the method according to any one of (1) to (10) above.

(12) Implants of the porous and composite materials according to (11) above.

DISCLOSURE OF THE INVENTION

1. A process for producing porous and composite materials

The present invention relates to a process for producing porous and composite materials of at least one calcium salt selected from calcium phosphate, calcium carbonate, and hydroxyapatite and collagen.

In the production process according to the present invention, composite materials having a large number of pores (porous and composite materials) are produced by cooling a complex containing at least one calcium salt selected from calcium carbonate, calcium phosphate, and hydroxyapatite and collagen, at least a part of which is gelatinized, to gelate the gelatin; freezing it; and then lyophilizing the resultant. Surface crosslinking between collagens is introduced to the resulting porous and composite materials. This allows the porous and composite materials to have mechanical strengths that are suitable for implants.

The production process according to the present invention is hereafter described in detail.

1.1 A complex containing calcium salt and collagen, at least a part of which is gelatinized The porous and composite materials according to the present invention are produced from a complex of at least one calcium salt selected from calcium phosphate, calcium carbonate, and hydroxyapatite and collagen, at least a part of which is gelatinized.

1) Calcium salt (hydroxyapatite)

The "calcium salt" that constitutes the complex of the present invention is at least one selected from calcium phosphate, calcium carbonate, and hydroxyapatite. In particular, hydroxyapatite is the most preferable.

Hydroxyapatite is a compound generally composed of $Ca_5(PO_4)_3OH$, and it includes a group of compounds referred to as calcium phosphate such as $CaHPO_4$, $Ca_3(PO_4)_2$, $Ca_4(PO_4)_2$, $Ca_{10}(PO_4)_6(OH)_2$, $CaP_4O_{11}$, $Ca(PO_3)_2$, $Ca_2P_2O_7$, and $Ca(H_2PO_4)_2 \cdot H_2O$. Also, hydroxyapatite is basically composed of a compound represented by formula $Ca_5(PO_4)_3OH$ or $Ca_{10}(PO_4)_6(OH)_2$, and a part of the Ca component may be substituted with at least one member selected from Sr, Ba, MG, Fe, Al, Y, La, Na, K, H, and the like. A part of the ($PO_4$) component may be substituted with at least one member selected from $VO_4$, $BO_3$, $SO_4$, $CO_3$, $SiO_4$, and the like. A part of the (OH) component may be substituted with at least one member selected from F, Cl, O, $CO_3$, and the like. Some of these components may be deficient. In general, a part of apatite $PO_4$ and OH components in biological bones are substituted with $CO_3$. Accordingly, the aforementioned components may be partially substituted by inclusion of $CO_3$ in the air (about 0% to 10% by mass) during the production of the porous and composite materials of the present invention.

Hydroxyapatite is generally microcrystalline, noncrystalline, or crystalline. Alternatively, it may exist in the form of an isomorphic solid solution, substitutional solid solution, or interstitial solid solution. The atomic ratio of calcium/phosphorus (Ca/P) in this "hydroxyapatite" is preferably in the range between 1.3 and 1.8. In particular, the range between 1.5 and 1.7 is more preferable. When the atomic ratio is in the range between 1.3 and 1.8, the composition and the crystal structure of apatite in the product (a calcium phosphate compound) can be similar to those in bones of vertebrates. This improves biocompatibility and bioabsorbability.

2) Collagen

The "collagen" that constitutes the complex of the present invention includes a general collagen molecule that has the triple helix structure and gelatinized "denatured collagen," the triple helix structure of which is destroyed by thermal or other treatment.

At present, about 20 different molecular species of collagens are known to be present in a wide variety of animal tissues ranging from mammalians to fish. These are generically denoted as "collagens." The species, the location of tissue, the age, and other factors regarding the animal that is a starting material for the collagen used in the present invention are not particularly limited, and any type of collagen can be used. In general, collagens obtained from skin, bones, cartilage, tendons, organs, or the like of mammalians (such as cow, pig, horse, rabbit, or mouse) and birds (such as chicken) are used. Also, collagen-like proteins obtained from skin, bones, cartilage, fins, scales, organs, or the like of fish (such as cod, left-eyed flounder, right-eyed flounder, salmon, trout, tuna, mackerel, sea bream, sardine, or shark) may be used as starting materials. Alternatively, collagen may be obtained by gene recombination techniques instead of by extraction from animal tissues.

Among the molecular species of collagens, the quantity of type I collagens is the largest, and they have been well studied. In general, when simple reference is made to a "collagen," it often indicates type I collagen. The molecular species of the collagen used in the present invention is not particularly limited, and type I collagen is preferably a main component. Further, collagen may be prepared by adequately subjecting an amino acid residue of the collagen protein to chemical modification such as acetylation, succination, maleylation, phthalation, benzoylation, esterification, amidation, or guanidination.

An example of a process for preparing collagen is extraction from the aforementioned starting material (excluding the gene recombination technique) with the aid of a neutral buffer or dilute acid such as hydrochloric acid, acetic acid, or citric acid. Collagen obtained with the aid of the former is referred to as neutral salt-soluble collagen, and that obtained with the aid of the latter is referred to as acid-soluble collagen. However, the amount of collagen extracted is small in either case, and a majority thereof remains as insoluble collagen. Enzyme solubilization and alkali solubilization are known as methods for solubilizing this insoluble collagen. Collagen obtained by the former method is referred to as enzyme-solubilized collagen, and that obtained by the latter method is referred to as alkali-solubilized collagen. Both can be solubilized as molecular collagens with yields of substantially 100%.

The method for preparing collagen used in the present invention (extraction type) is not particularly limited. If the molecular weight of solubilized collagen is large, however, the strength of a complex becomes insufficient because of steric hindrance. Accordingly, the use of monomeric (monomolecular) collagen is preferable. In enzyme-solubilized collagen and alkali-solubilized collagen, the monomeric collagen content is high, and non-helical regions (telopeptides) having a majority of collagen antigenicity are selectively degraded and removed during the step of production. Thus, they are particularly adequate for the organic or inorganic porous and composite materials of the present invention. If these non-helical regions are degraded and removed from collagen, this collagen is referred to as "atelocollagen."

The isoionic point of enzyme-solubilized collagen is different from that of alkali-solubilized collagen. The isoionic point is the pH level where both positive and negative charges, which are derived from a dissociable group inherent to a protein molecule, repel each other. In the case of collagen, when the pH level approaches the region of the isoionic point, solubilized collagen is known to become fibrous. In general, the isoionic point of the enzyme-solubilized collagen is between pH 8 and 9, and that of the alkali-solubilized collagen is between pH 4 and 5. In the present invention, it is preferable to use the enzyme-solubilized collagen in a reaction vessel maintained between pH 7 and 11 wherein the fiberization and self-organization is likely to occur. Examples of enzymes for solubilization include pepsin, trypsin, chymotrypsin, papain, and pronase. Pepsin and pronase are preferably used from the viewpoint of easy handleability after the enzyme reaction.

3) A complex containing calcium salt and collagen

At least a part of the collagen in the complex used in the present invention must be gelatinized. The term "gelatin" refers to denatured collagen that is obtained by cleavage of salt bonds or hydrogen bonds between peptide chains of collagen by treatment with boiling water or the like, followed by irreversible denaturation into a water-soluble protein. As mentioned above, the term "collagen" used herein include this gelatinized collagen. Gelatinization of collagen may be realized by gelatinizing a part of the collagen constituting a complex containing calcium salt and collagen. Alternatively, gelatinized collagen such as a commercialized solution of gelatin powders may be externally added to the complex.

In the production process according to the present invention, a "complex containing calcium salt and collagen" is employed as a starting material for the reaction. Such a complex may be a commercialized one or may be prepared in accordance with a known technique. A preferable example of the complex is a "complex of hydroxyapatite and collagen." In particular, a "self-organized complex containing hydroxyapatite and collagen" is the most preferable. These complexes are described in detail in 2.3 below.

1.2 Gelatinization of collagen

Examples of processes for gelatinizing a part of the collagen constituting the complex containing calcium salt and collagen include a method wherein a physiological buffer such as PBS or Tris or water is added to the complex, and the resultant is then heated, and a method wherein a physiological buffer containing a minor amount of acid or water is added to the complex, and the resultant is then heated.

The amount of a buffer or water to be added is preferably about 24 to 60 ml per g of collagen (in the case of a complex, 25% of which is constituted by collagen, about 6 to 15 ml of buffer or water per g of the complex). By changing the amount of the buffer added, porosities, pore diameters, or strengths of the resulting porous and composite materials can be adequately controlled. When acid is added, a weak acid such as gluconic acid is preferably used together with a weak alkali such as calcium carbonate in order to control the pH level. The amount of gluconic acid used is preferably about 0.8 g to 4 g per g of collagen (in the case of a complex, 25% of which is constituted by collagen, about 200 mg to 1,000 mg of gluconic acid per g of the complex). The amount of alkali that is simultaneously added may be adequately determined in accordance with the amount of gluconic acid in order to bring the pH level to around 5.0.

When acid is not added, the reaction temperature is preferably between 40° C. and 50° C., and particularly preferably around 45° C. The reaction time is preferably about 60 to 120 minutes. When acid is added, the reaction temperature is preferably between 35° C. and 45° C., and particularly preferably around 40° C. The reaction time is preferably about 60 to 120 minutes. That is, collagen can be gelatinized at relatively low temperature by the method, which is carried out with the addition of acid.

By changing the reaction temperature or reaction time, the level of gelatinization can be varied, and the pore diameters or mechanical strengths of the resulting porous and composite materials can be adequately controlled. More specifically, if the reaction temperature is too low or the reaction time is too short, gelatinization is insufficient. This results in small pore diameters and lowered strengths of the porous and composite materials. In contrast, if the reaction temperature is too high or the reaction time is too long, excessive gelatinization occurs. This results in lowered strengths of the resulting porous and composite materials.

1.3 Freezing of a complex

Subsequently, a complex containing collagen, at least a part of which is gelatinized, is placed in an adequate mold and then allowed to freeze.

1) Cooling

The aforementioned complex after gelatinization has low viscosity in a heated state. If it is placed in a mold in that state, the complex is precipitated, and a porous complex having a homogenous structure cannot be obtained. Thus, the complex is preferably cooled for gelatinization and then placed in a mold. A method for cooling is not particularly limited. For example, the complex can be subjected to ice cooling, and cooling is continued until it becomes a jell or mousse.

During this step of cooling, gelatinized collagen is homogenously incorporated in a complex and solidified as a jell. Freezing thereof results in homogenous growth of ice crystals in the complex. These ice crystals become pores in the subsequent step of lyophilization. Thus, porous and composite materials having large pore diameters, high porosities, and specific mechanical strengths (elasticity) can be provided.

2) Internal crosslinking

Before the complex is placed in a mold, an adequate crosslinking agent is added to the complex in order to introduce internal crosslinking between collagens constituting the complex. This is preferable since the resulting porous body has larger pore diameters and a larger number of open pores.

The term "internal crosslinking" used herein refers to crosslinking that is introduced between collagens that are present in the complex. Crosslinking occurs either between ungelatinized collagens, between gelatinized collagens, or between ungelatinized collagen and gelatinized collagen. Crosslinking may occur at any portions of collagens. Particularly preferable crosslinking occurs between a carboxyl group and a hydroxyl group, between a carboxyl group and a $\epsilon$-amino group, or between $\epsilon$-amino groups.

Any method, such as chemical crosslinking using a crosslinking agent or condensing agent or physical crosslinking using $\gamma$ rays, ultraviolet rays, thermal dehydration, an electron beam, or the like, may be employed. Chemical crosslinking using a crosslinking agent is preferable.

Examples of crosslinking agents that can be used include: aldehyde crosslinking agents such as glutaraldehyde or formaldehyde; isocyanate crosslinking agents such as hexamethylene diisocyanate; carbodiimide crosslinking agents such as 1-ethyl-3-(3-dimethylaminopropyl)carbodiimide hydrochloride; polyepoxy crosslinking agents such as ethylene glycol diethyl ether; and transglutaminase, with glutaraldehyde being preferable. The amount of the crosslinking agent to be added is adequately determined in accordance with its type. In the case of glutaraldehyde, it is preferably 0.4 mg to 40 mg, and particularly preferably about 4 mg to 10 mg, per g of collagen before gelatinization (initial amount) (in the case of a complex, 25% of which is constituted by collagen, 0.1 mg to 10 mg, and particularly about 1 mg to 2.5 mg, per g of the complex).

3) Freezing

The cooled complex is allowed to freeze in accordance with a conventional technique. The freezing speed in a freezer is slowed in order to allow ice crystals to grow. These ice crystals become pores in the subsequent step of lyophilization. The pore sizes affect the strengths of the resulting porous and composite materials. Thus, the use of a refrigerator, the temperature of which can be subtly controlled, is more preferable from the viewpoint of the controllability of the freezing speed.

1.4 Lyophilization

The frozen complex is allowed to lyophilize in accordance with a conventional technique. During this step of lyophilization, numerous ice crystals, which were formed in the complex during the step of freezing, become pores. Thus, porous and composite materials having desirable porosities and pore diameters are obtained.

1.5 Surface crosslinking

The mechanical strengths of the resulting porous and composite materials can be enhanced by introducing surface crosslinking between collagens. The term "surface crosslinking" refers to crosslinking that is introduced between collagens that are present on the surface of the porous and composite materials.

Any method, such as chemical crosslinking using a crosslinking agent or condensing agent or physical crosslinking using γ rays, ultraviolet rays, thermal dehydration, an electron beam, or the like, may be employed for surface crosslinking. Examples of crosslinking agents include: aldehyde crosslinking agents such as glutaraldehyde or formaldehyde; isocyanate crosslinking agents such as hexamethylene diisocyanate; carbodiimide crosslinking agents such as 1-ethyl-3-(3-dimethylaminopropyl)carbodiimide hydrochloride; polyepoxy crosslinking agents such as ethylene glycol diethyl ether; and transglutaminase. The amount of the crosslinking agent to be used is adequately determined in accordance with its type. It is preferably at least 1 μmol per g of the complex.

Crosslinking as mentioned above may occur at any portions of collagens. Particularly preferable crosslinking occurs between a carboxyl group and a hydroxyl group, between a carboxyl group and a ε-amino group, or between ε-amino groups. Crosslinking is preferably introduced in at least 1%, and more preferably at least 5%, of reactive functional groups. This is because sufficient mechanical strengths cannot be expected if crosslinking is insufficient. Attention should be given to the use of a crosslinking agent since the excessive use of a crosslinking agent disadvantageously embrittles a complex.

Among the aforementioned methods for crosslinking, chemical crosslinking using a crosslinking agent such as glutaraldehyde is particularly preferable from the viewpoints of controllability of the level of crosslinking and bioadaptability of the resulting complex. Chemical crosslinking can be performed by immersing the porous and composite materials obtained in the section above in a solution containing a crosslinking agent.

A method for crosslinking using glutaraldehyde is hereafter described as a preferable embodiment of the present invention. At the outset, the porous and composite materials obtained in the section above are immersed in a solution containing 0.001% to 1%, and preferably about 0.005% to 0.1%, glutaraldehyde (degassing and aspiration). Use of 50% to 100% ethanol as a solvent is preferable since crosslinking density is enhanced. Conditions for immersion are adequately determined in accordance with the concentration of glutaraldehyde. Preferably, it is generally slowly carried out over the course of a period of approximately 60 minutes to 5 hours at room temperature or lower temperature in order to allow the crosslinking to homogenously occur. After the crosslinking, the porous and composite materials are washed with pure water to remove excess glutaraldehyde. Further, remaining glutaraldehyde may be preferably neutralized with the use of a glycine solution or the like. The porous and composite materials may be further lyophilized after crosslinking.

Thus, the porous and composite materials can be provided with desirable mechanical strengths by introducing surface crosslinking therein. The degradation rate in an organism can be controlled based on the level of crosslinking to be introduced.

1.6 Others

In addition, adequate modifications or additional steps can be added to the aforementioned steps within the scope of the present invention. For example, addition of polysaccharides such as hyaluronic acid prior to the crosslinking can increase the points of crosslinking and enhance the mechanical strengths. Alternatively, polysaccharides such as hyaluronic acid can be added instead of gelatinized collagen, crosslinking can be introduced thereto, and the resultant can be allowed to gelatinize and freeze. Thus, a porous body having large pore diameters and high porosities can be obtained.

A wide variety of treatments can be applied in order to enhance the strengths of the porous and composite materials after surface crosslinking. For example, the surfaces of the porous and composite materials may be coated with hydroxyapatite and collagen by immersing them in a slurry of a complex of hydroxyapatite and collagen. The surfaces of the porous and composite materials may be coated with hydroxyapatite by immersing them in a slurry of hydroxyapatite. Alternatively, hydroxyapatite may be precipitated not only on the surfaces but also on the insides of the porous and composite materials by alternate immersion in calcium and phosphorus.

2. The porous and composite materials of the present invention 2.1 Properties of the porous and composite materials (porosities, pore diameters, and mechanical strengths)

The porous and composite materials obtained by the method according to the present invention have high porosities, large pore diameters, and adequate mechanical strengths. The porosities of the porous and composite materials obtained under preferable conditions are 80% to 95%, and the pore diameters thereof are about 50 μm to 2,000 μm. However, the porosities or pore diameters of the porous and composite materials can be adequately changed by altering the amount of a buffer, the reaction temperature, and the reaction time in the step of gelatinization, the freezing speed in the step of freezing, or other factors. Accordingly, porous and composite materials having desirable porosities and pore diameters can be obtained by changing the aforementioned conditions. Further, conditions for internal or surface crosslinking can be adequately determined to obtain porous and composite materials having desirable strengths.

2.2 Evaluation of properties of porous and composite materials

The porosities and the pore diameters of the porous and composite materials of the present invention can be measured and evaluated by, for example, image analysis of electron micrographs. Mechanical strengths can be evaluated based on, for example, the three-point bending strength or the Young's modulus, determined based thereon. Alternatively, the strength can be evaluated based on functional analysis of operability when it is actually used, such as during transplantation tests.

2.3 Self-organized porous and composite materials containing hydroxyapatite and collagen A preferable example of the porous and composite material of the present invention is a microporous and composite material containing hydroxyapatite and collagen in which the c-axis of hydroxyapatite is oriented along with collagen fiber.

This composite material is produced using a self-organized complex containing hydroxyapatite and collagen as a starting material. The term "self-organized" generally refers to the "formation of a specific organization through the aggregation of homologous or heterologous atoms, molecules, fine particles, or the like by non-covalent binding interaction" (Seikagaku Jiten (Dictionary of Biochemistry), Tokyo Kagaku Dozin Co., Ltd.). In the present invention, this term particularly refers to the fact that hydroxyapatite having an apatite structure forms an orientation that is specific to biological bones along collagen fibers. That is, a microporous structure in which the c-axis of hydroxyapatite is oriented along collagen fibers is formed. Self-organized complexes containing hydroxyapatite and collagen can be produced in accordance with, for example, the method of Kikuchi et al. (Kikuchi, S. et al., J. Biomater., 22 (13)(2001), 1705–1711, S. Itoh et al., J. Biomed Mater Res. (2001), 445–453).

This microporous structure in which the c-axis of hydroxyapatite is oriented along collagen fibers is partially maintained during the production step according to the present invention. Accordingly, the resulting porous and composite materials have microporous structures similar to those of biological bones.

2.4 Others

The porous and composite materials of the present invention can contain other components within the scope of the present invention. Examples of such components include inorganic salts such as St, Mg, and $CO_3$, organic substances such as citric acid and phospholipids, Bone Morphogenetic Proteins, and agents such as an anti-cancer agent.

3. A method for utilizing porous and composite materials 3.1 Implants

The porous and composite materials obtained by the method of the present invention have high porosities, and each component thereof is biodegradable. Accordingly, they are easily penetrated by cells and they are excellent in bone conductivity because they contain hydroxyapatite and collagen. Further, adequate mechanical strengths and retentivity in organisms (adequate rate of biodegradation) can be controlled by crosslinking. Accordingly, the porous and composite materials of the present invention are suitable for implants that are used in the field of orthopedics such as bone fillers or implants that are used in the field of dentistry.

The configurations and forms of the aforementioned implants are not particularly limited. Implants can take any desired configurations and forms in accordance with their applications. For example, they can be blocks, pastes, films, particles, or sponges.

The porous and composite materials of the present invention have low compressive strengths. Upon moisture absorption, they become elastic as sponges, they are less likely to collapse even with the application of forces strong enough to deform (crush) them, they reabsorb moisture, and they rapidly regain their original forms. This feature results in an excellent operability at the time of surgical operations. When the porous and composite materials of the present invention are used as implants by making use of the aforementioned feature, they may be once immersed in an adequate liquid such as physiological saline before use.

3.2 Drug carrier for sustained-release (cell carrier, DNA carrier)

The porous and composite materials of the present invention have large surface areas of hydroxyapatite or the like that are capable of adsorbing a protein, DNA, or the like and the densities thereof are not too high. Thus, penetration and release of an agent or the like can easily occur. Accordingly, the porous and composite materials of the present invention can be used as a drug carrier for sustained-release. Drug carriers for sustained-release using the porous and composite materials of the present invention have high drug adsorptivity, and their forms are well preserved. The aforementioned drug carriers for sustained-release have higher drug-adsorptivity and penetrability by cells compared with a conventional block of hydroxyapatite and collagen. The drug carriers for sustained-release using the porous and composite materials of the present invention can prevent carcinoma recurrence and induce the generation of hard tissue of the organism by, for example, impregnating an anti-cancer agent or the like therein to use it for reconstructing bones resected due to osteogenic sarcoma or other reasons.

The aforementioned carriers can be used as carriers not only for drugs but also for cells or DNA. For example, when they are used as cell carriers, cells are introduced into the carrier under negative pressure by suction, and the resultants are applied to a site of interest.

3.3 Media for cell culture (scaffold)

The porous and composite materials of the present invention can be used as media for cell culture (scaffold) through the utilization of their high porosities, large pore diameters, and flexibilities. For example, highly bioactive cytokines are incorporated, the resultant is used as media to conduct tissue culture in an environment similar to that of organisms to which force, electricity, or the like is applied or in vivo. Thus, tissues such as bone marrow or liver tissues can be reconstructed.

More specifically, the porous and composite material obtained by the present invention can be put to a wide range of applications. Examples thereof include artificial bones, artificial joints, cements for tendons and bones, dental implants, percutaneous terminals for catheters, drug carriers for sustained-release, cell carriers, DNA carriers, media for cell culture, chambers for bone marrow induction, and chambers or base materials for tissue reconstruction.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODES FOR CARRYING OUT THE INVENTION

The present invention is hereafter described in more detail with reference to the examples, although the technical scope of the present invention is not limited thereto.

EXAMPLE 1

Preparation of a Hydroxyapatite/Collagen (HAp/Col) Porous Body

1. Production of HAp/Col Composite Materials (1) Gelatinization of Collagen

In accordance with the method of Kikuchi et al. (M. Kikuchi et al., Biomater., 22 (13)(2001), 1705–1711), 500 mg of HAp/Col complex powders (HAp:Col=3:1, lyophilized powders) were prepared. PBS (6 ml) was added thereto, followed by mixing. The resultant was incubated at 45° C. for 90 minutes, and a part of the collagen was allowed to gelatinize.

(2) Internal Crosslinking

The gelatinized HAp/Col complex was allowed to cool. When the complex became runny, a mixture of 2 µl of 25% glutaraldehyde with 0.5 ml of PBS was added thereto, and the resultant was placed in a mold, followed by ice cooling.

(3) Freezing

The ice-cooled HAp/Col complex was kept in the mold, placed in a 450 ml plastic case in that state, and then sealed. The resultant was allowed to freeze in a freezer at −20° C.

(4) Lyophilization

Figure 1:
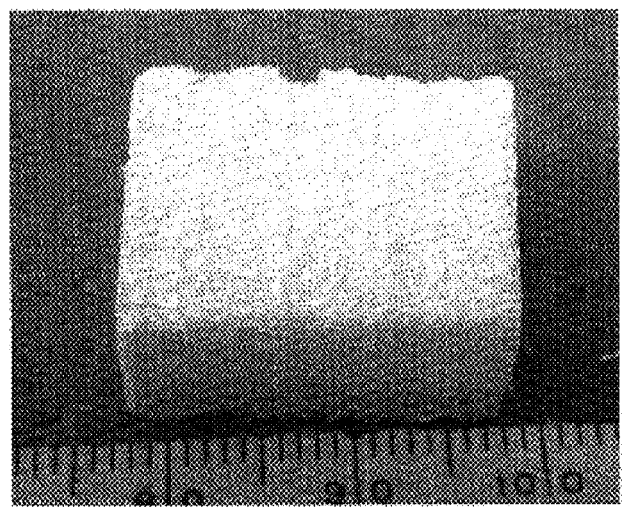
FIG. 1 shows photographs of the HAp/Col porous body prepared in Example 1 (A: a complete photograph of the porous body; B: an enlarged photograph).
Figure 1:
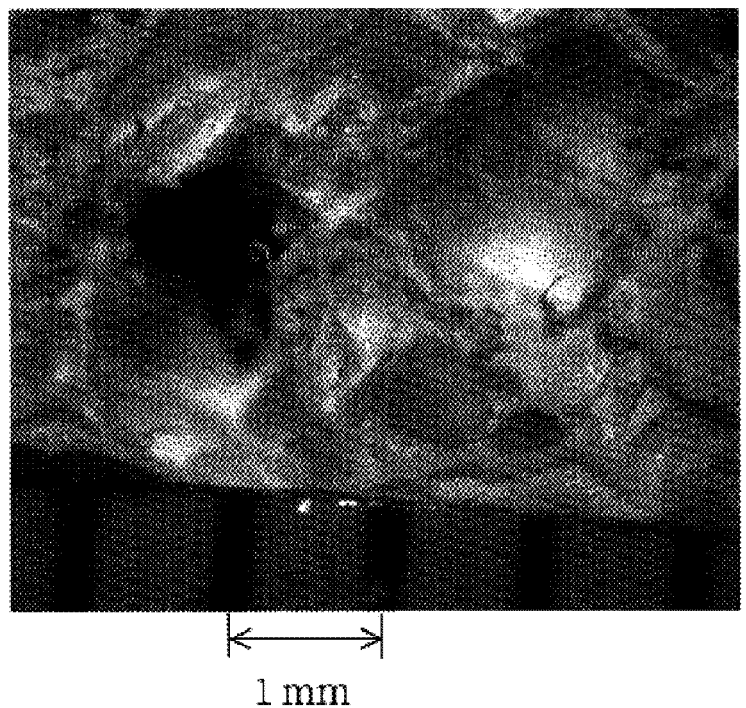

The frozen HAp/Col complex was lyophilized in accordance with a conventional technique. The resulting porous body is shown in FIG. 1.

(5) Surface Crosslinking

The lyophilized complex was immersed in 50% ethanol containing 0.01% glutaraldehyde for 2 hours to introduce crosslinking between collagens on the surface of the porous body (surface crosslinking). After the reaction, the complex was washed with pure water to remove remaining glutaraldehyde. A glycine solution was further added thereto to neutralize the remaining glutaraldehyde. Thereafter, the complex was washed with pure water and allowed to dry to obtain the HAp/Col porous body of interest.

2. Evaluation of the HAp/Col Porous Body

As is apparent from FIG. 1, the resulting HAp/Col porous body contained numerous bubbles having relatively large sizes (pore sizes: approximately 50 to 2,000 µm). The porosities thereof were deduced to be approximately 80% to 95%. The surface-crosslinked HAp/Col porous body became an elastic sponge upon immersion in water. Even though it was deformed with the application of external force, it could rapidly regain its original form when the force was relieved.

EXAMPLE 2

Examination of Conditions for Producing the HAp/Col Porous Body

Conditions in the production step in Example 1 were varied, and the pore diameters and the porosities of the resulting porous bodies were examined. These porous bodies were not subjected to surface crosslinking.

1. Examinations of conditions for gelatinization (1) Incubation Time

Figure 2:
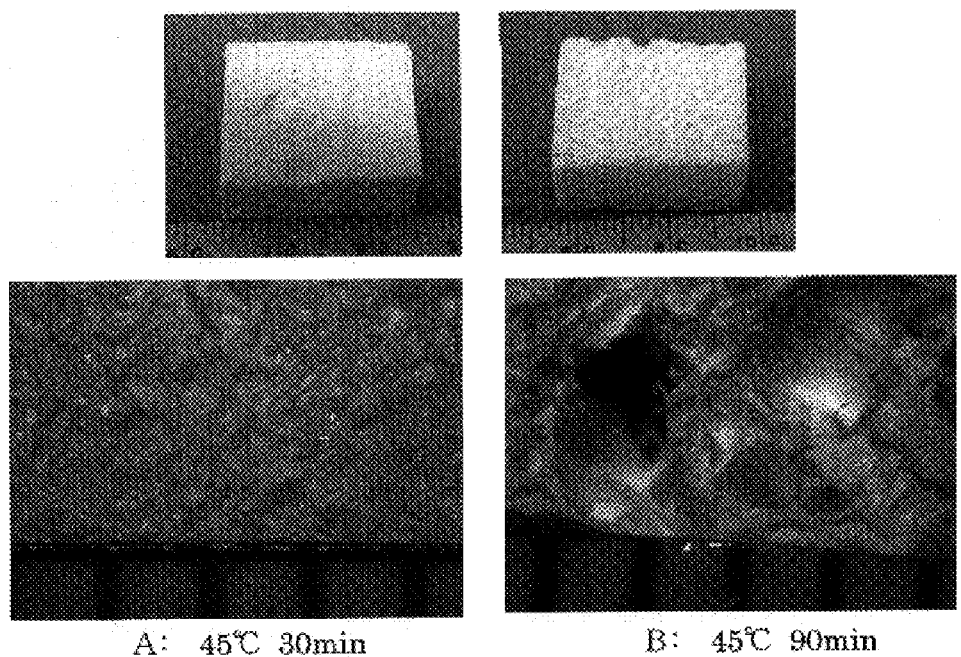
FIG. 2 shows photographs of the porous body prepared when the incubation time in the step of gelatinization is 30 minutes or 90 minutes (A: 30 minutes; B: 90 minutes).

The HAp/Col porous body was prepared in the same manner as in Example 1 except that the incubation time in the step for gelatinization was changed to 30 minutes. The resultant was compared with the HAP/Col porous body obtained in Example 1 (FIG. 2).

As a result, the porous body that was prepared with an incubation time of 30 minutes had very small pore diameters compared with that prepared with an incubation time of 90 minutes.

(2) The Amount of PBS

Figure 3:
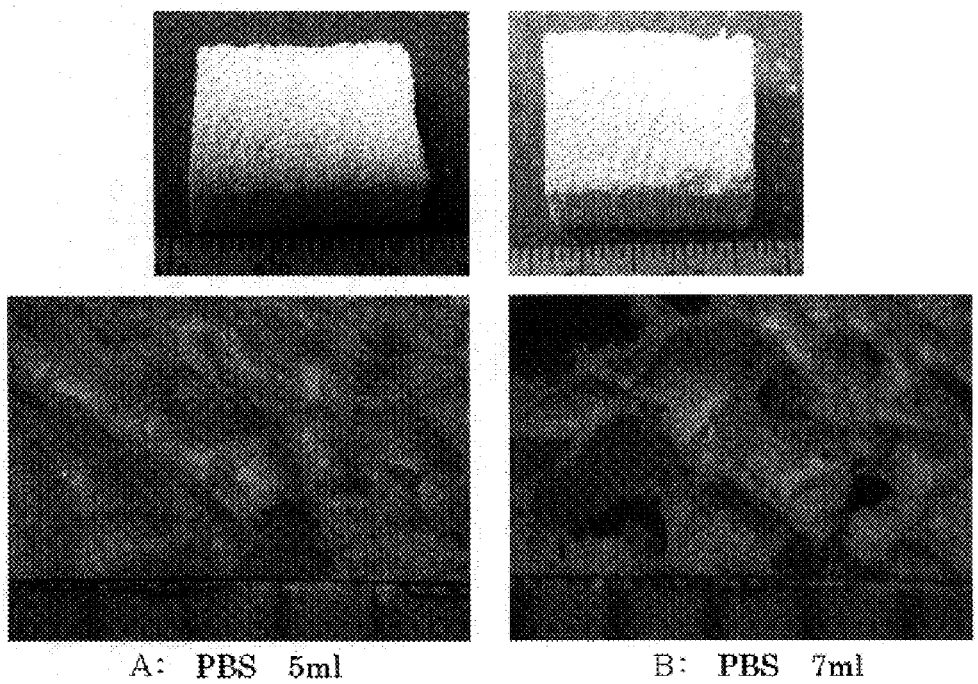
FIG. 3 shows photographs of the porous body prepared when the amount of PBS added in the step of gelatinization is 5 ml or 7 ml (A: 5 ml; B: 7 ml).

The HAp/Col porous body was prepared in the same manner as in Example 1 except that the amount of PBS added in the step of gelatinization was changed to 5 ml or 7 ml. The resultant was compared with the HAP/Col porous body obtained in Example 1 (FIG. 3).

As a result, a porous body having sufficiently large pore diameters was obtained with the use of 5 ml, 6 ml, or 7 ml of PBS. When the amount of PBS was 7 ml, the pore diameter was slightly larger than that obtained with the use of 5 ml or 6 ml of PBS. The porous body was more flexible when it was immersed in water.

(3) Mixing of Ungelatinized HAp/Col

Figure 4:
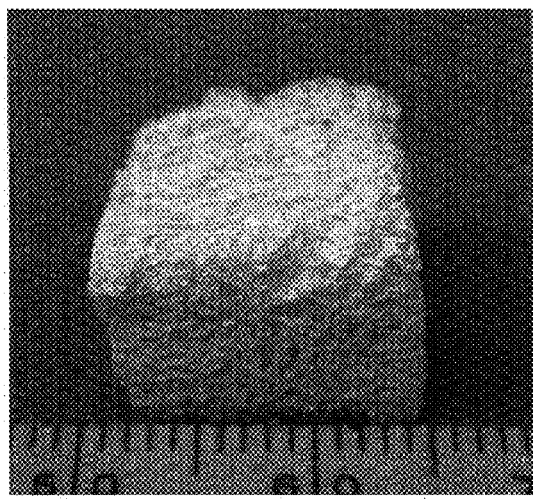
FIG. 4 shows photographs of the porous body prepared by mixing ungelatinized HAp/Col (A: a complete photograph of the porous body; B: an enlarged photograph).
Figure 4:
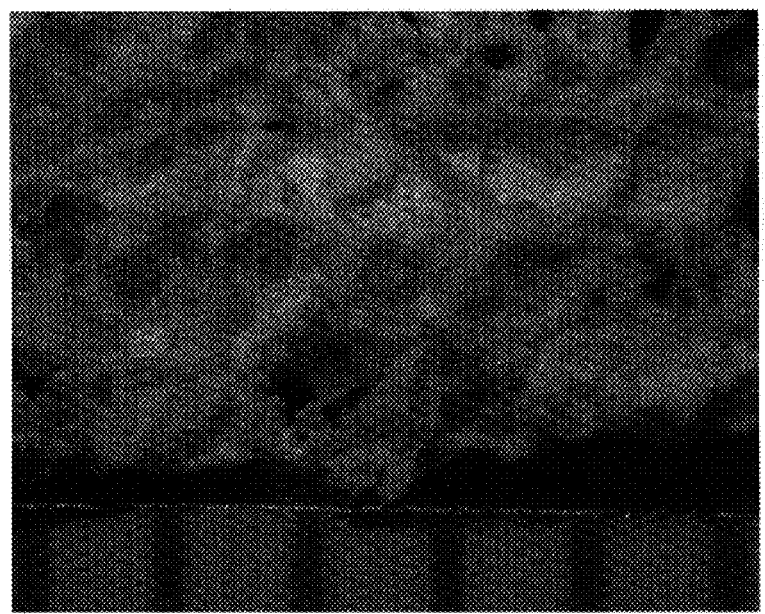

In the step of gelatinization, PBS was added to 30% of HAp/Col (500 mg), and the resultant was incubated at 45° C. for 90 minutes. PBS was added to the remaining 70% thereof, and the resultant was incubated at 40° C. for 60 minutes (gelatinization hardly occurred at 40° C. for 60 minutes). Thereafter, these were mixed with each other to prepare the HAp/Col porous body in the same manner as in Example 1 (FIG. 4).

As a result, a porous body having sufficient pore diameters was obtained by this method. This porous body had a larger number of continuous pores than the porous body obtained in Example 1.

(4) Addition of Acid

In the step of gelatinization, 300 mg of gluconic acid and 83 mg of calcium carbonate were added to 4 ml of PBS, and the resultant was incubated at 40° C. for 90 minutes. The porous body was prepared in the same manner as in Example 1 except for the above-stated condition.

As a result, gelatinization occurred at 40° C. when acid was added, and a porous body having larger pore diameters was obtained.

2. Examination of Conditions for Internal Crosslinking

Figure 5:
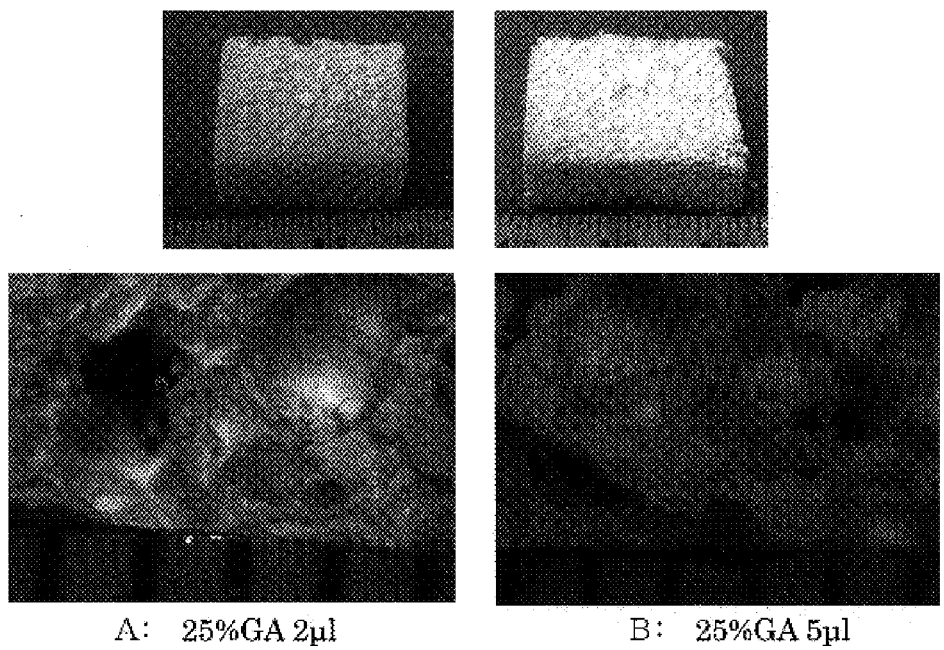
FIG. 5 shows photographs of the porous body prepared when the amount of GA added in the step of internal crosslinking is 2 µl or 5 µl (A: 2 µl of 25% GA; B: 5 µl of 25% GA).

The HAp/Col porous body was prepared in the same manner as in Example 1 except that the amount of 25% glutaraldehyde added in the step of internal crosslinking was changed to 5 μl. The resultant was compared with the HAP/Col porous body obtained in Example 1 (FIG. 5).

As a result, the porous body prepared with the addition of 5 μl of 25% glutaraldehyde and then immersed in water was harder and had a larger number of continuous pores compared with the porous body prepared with the addition of 2 μl of 25% glutaraldehyde and similarly immersed in water.

4. Examination of Conditions for Freezing

Figure 6:
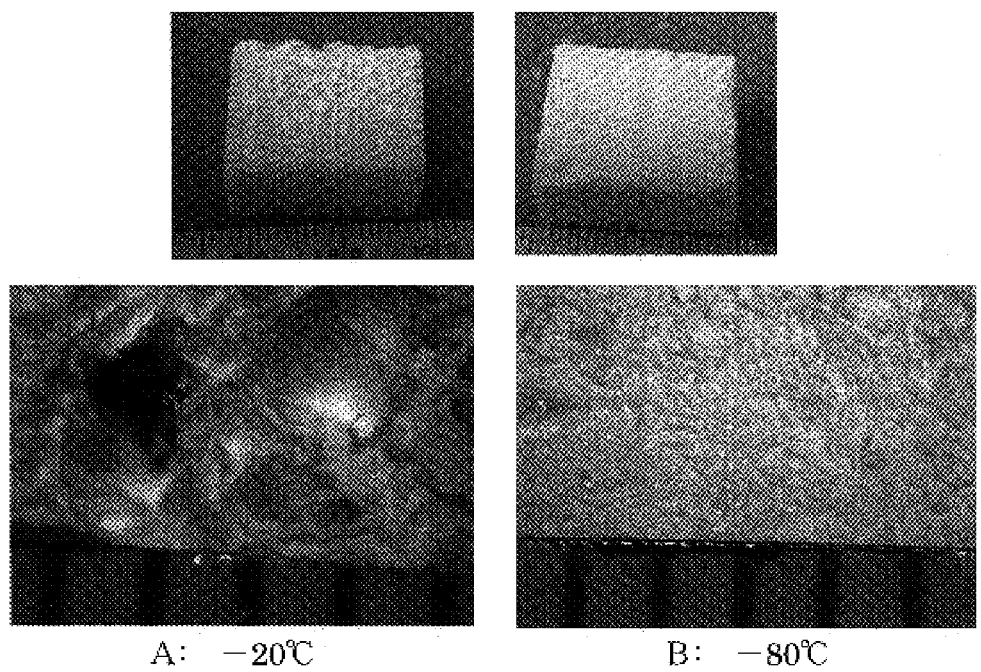
FIG. 6 shows photographs of the porous body prepared when the freezing temperature is −20° C. or −80° C. (A:−20° C.; B:−80° C.).
Figure 7:
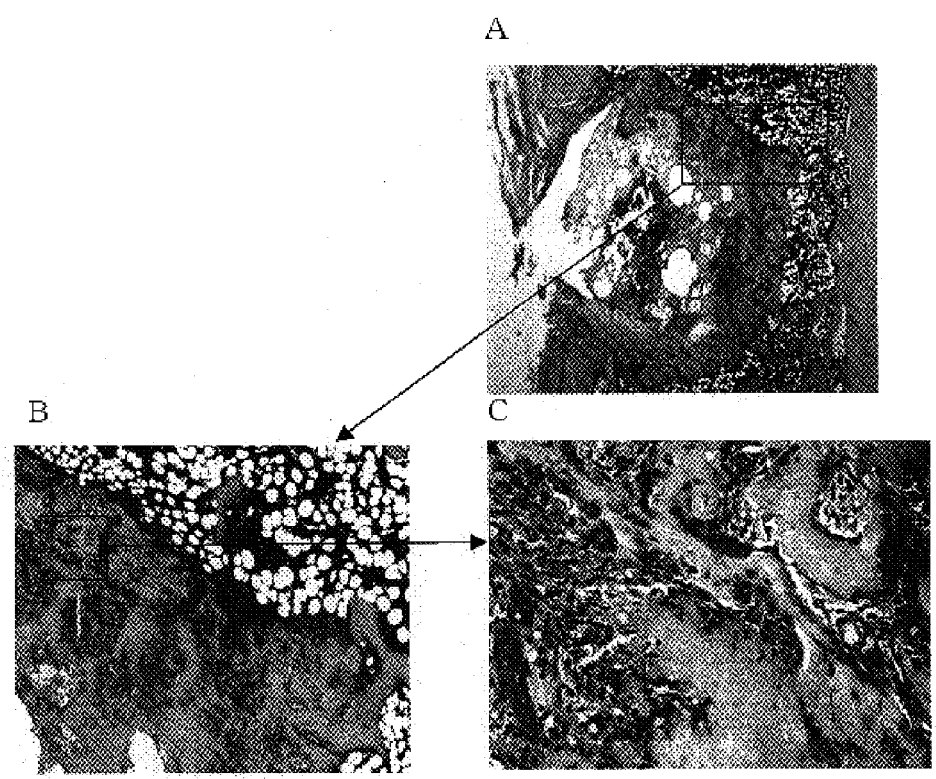
FIG. 7 shows images of HE staining one week after the transplantation of "an HAp/Col porous body that is surface-crosslinked with 0.01% GA and internally crosslinked" to a rat thighbone in Example 3.
Figure 8:
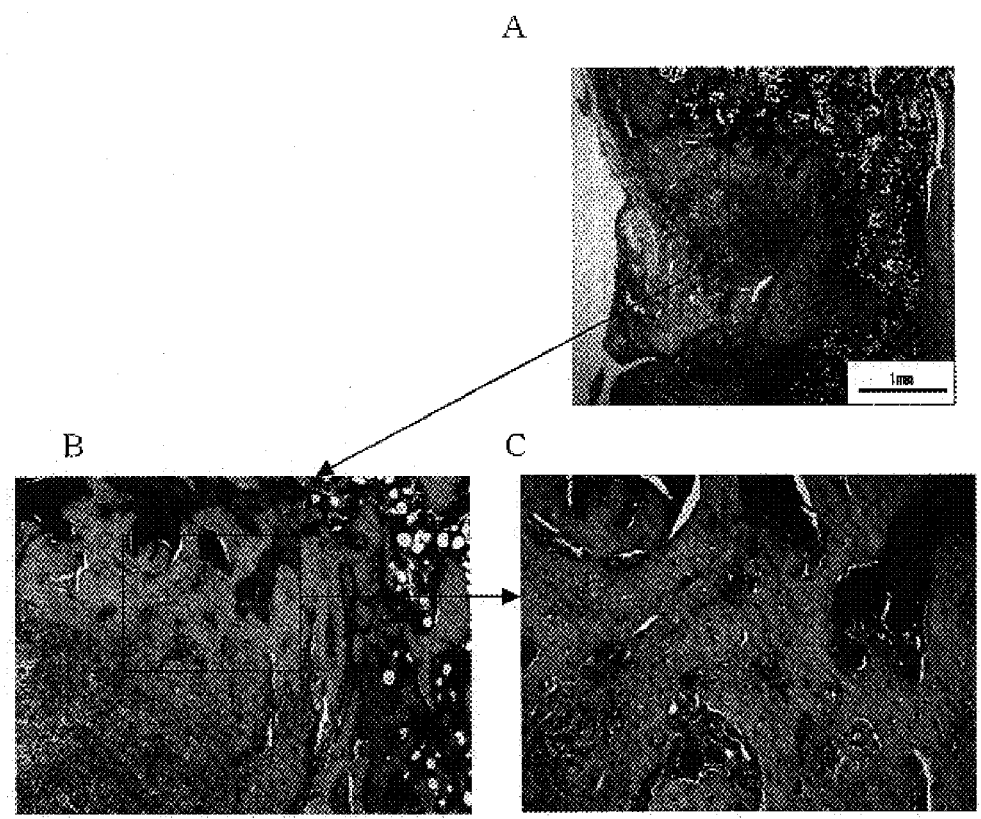
FIG. 8 shows images of HE staining three weeks after the transplantation of "an HAp/Col porous body that is surface-crosslinked with 0.01% GA and internally crosslinked" to a rat thighbone in Example 3.
Figure 9:
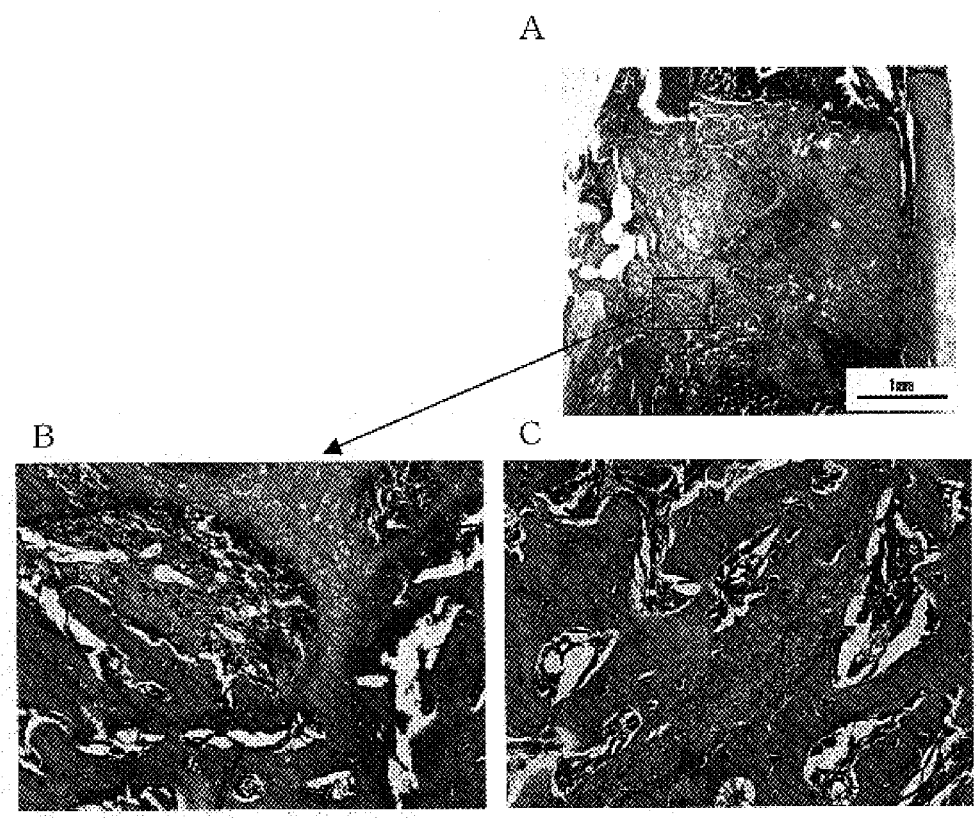
FIG. 9 shows images of HE staining two weeks after the transplantation of "an HAp/Col porous body that is surface-crosslinked with 0.01% GA and internally crosslinked" to a rat thighbone in Example 3.
Figure 10:
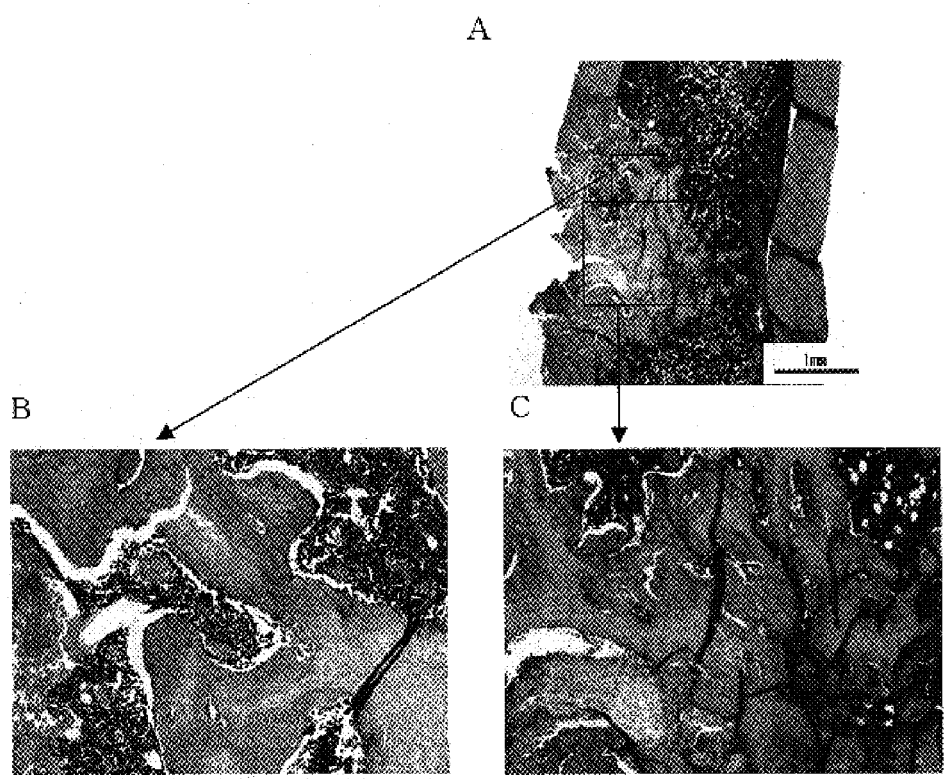
FIG. 10 shows images of HE staining four weeks after the transplantation of "an HAp/Col porous body that is surface-crosslinked with 0.01% GA and internally crosslinked" to a rat thighbone in Example 3.
Figure 11:
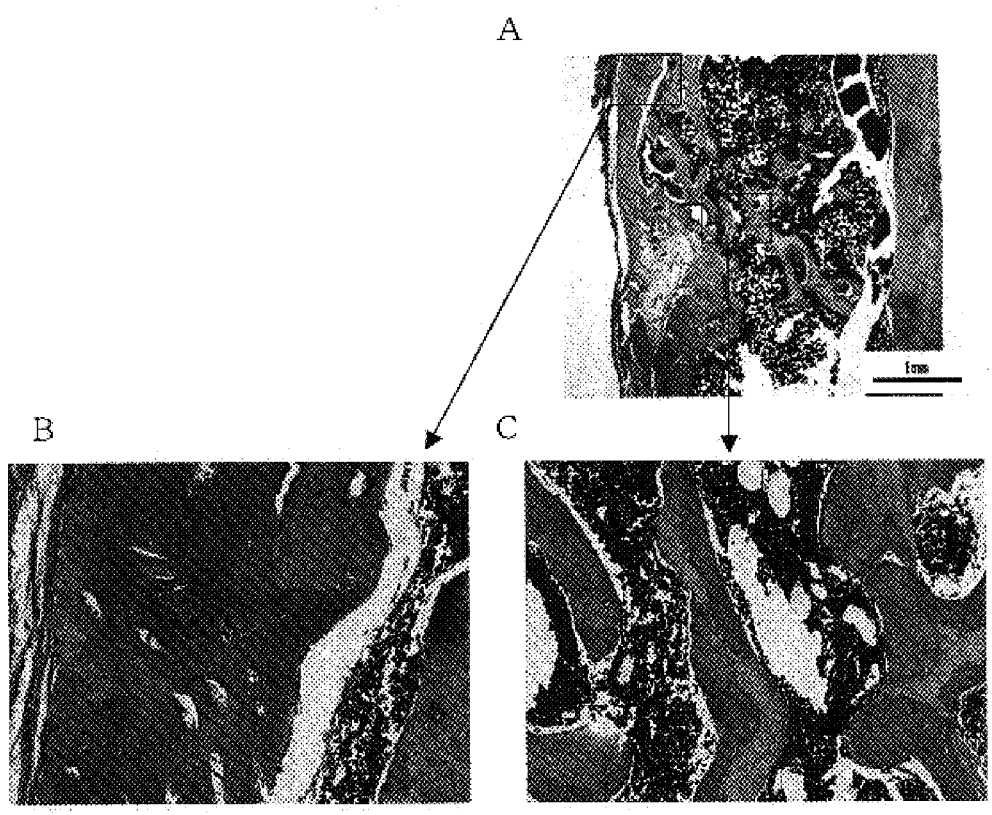
FIG. 11 shows images of HE staining six weeks after the transplantation of "an HAp/Col porous body that is surface-crosslinked with 0.01% GA and internally crosslinked" to a rat thighbone in Example 3.
Figure 12:
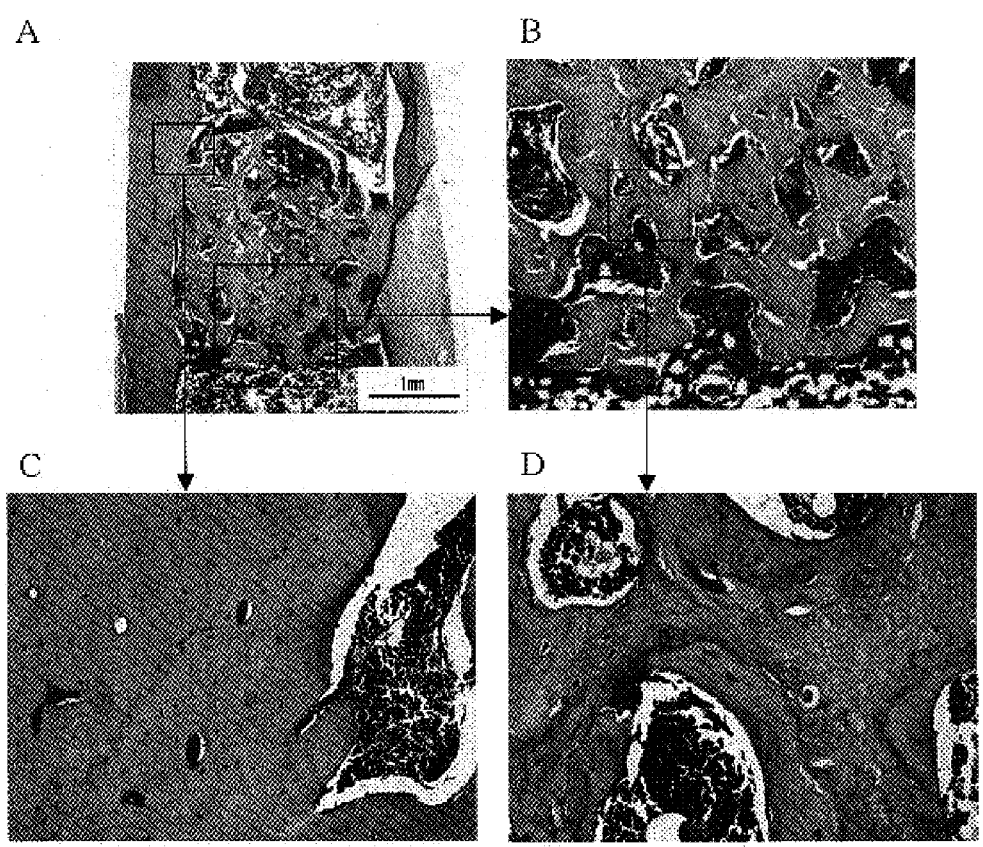
FIG. 12 shows images of HE staining six weeks after the transplantation of "an HAp/Col porous body that is surface-crosslinked with 0.05% GA" to a rat thighbone in Example 3.

The HAp/Col porous body was prepared in the same manner as in Example 1 except that the HAp/Col complex was allowed to freeze in a freezer at −80° C. without being placed in a case in the step of freezing. The resultant was compared with the HAP/Col porous body obtained in Example 1 (FIG. 6).

As a result, the porous body prepared by freezing at −80° C. had very small pore diameters compared with that prepared by freezing at −20° C.

Example 3

Experimentation for Transplanting the HAp/Col Porous Body to a Rat Thighbone

1. Preparation of Implants for Transplantation

In accordance with the method of Kikuchi et al., 500 mg of HAp/Col complex powders (HAp:Col=3:1) were prepared. PBS (4 ml), 300 mg of gluconic acid, and 83 mg of calcium carbonate were added thereto, and the mixture was incubated at 40° C. for 90 minutes for gelatinization. The gelatinized complex was allowed to freeze in a freezer at −20° C., and further lyophilized to obtain the HAp/Col porous body. The resulting porous body was immersed in a solution of 0.01% glutaraldehyde for 2 hours to introduce crosslinking between collagens on the surface of the complex (surface crosslinking).

Porous bodies were prepared under the above conditions. One type thereof was provided with internal crosslinking in the same manner as in Example 1, and another type was provided with surface crosslinking introduced with 0.5% glutaraldehyde (GA).

The prepared porous bodies were cut into 2×2×3 mm portions to prepare implants to be transplanted into rat thighbones.

2. Transplantation into rat thighbones

A hole (diameter: approximately 3 mm) was provided in the distal part of a Wistar rat thighbone, and the prepared implants were transplanted thereinto. The implants were taken out 1, 2, 3, 4, and 6 weeks after the transplantation and stained with hematoxylin and eosin for observation (FIGS. 7 to 12).

3. Results (1) HAp/Col Porous Body Surface-crosslinked with 0.01% GA

This porous body had lower porosity and a smaller number of continuous pores compared with the porous body of (2), which was subjected to internal crosslinking. Thus, penetrability by cells was less sufficient. With the elapse of time, however, implants were absorbed, and good bone formation was observed.

One week after the transplantation, good cell penetration in the vicinity or formation of neonatal bones was observed in a part thereof (FIGS. 7B, 7C). In other parts, there were pores which cells did not penetrate (FIG. 7A). Cell penetration was enhanced 2 weeks after the transplantation, and formation of neonatal bones that were in contact with the implants was observed. Three weeks after the transplantation, cell penetration and formation of neonatal bones were further enhanced in parenchyma (FIGS. 8A, 8C), and implants were significantly decreased because of absorption as neonatal bones were formed (FIG. 8B).

(2) HAp/Col Porous Body Surface-crosslinked with 0.01% GA and Internally Crosslinked The porous body to which internal crosslinking had been applied had somewhat larger pore diameters and the penetration by cells was better compared with the porous body of (1). While good cell penetration and formation of neonatal bones around the implants were observed 2 weeks after the transplantation (FIG. 9A), absorption of implants by osteoclasts was observed (FIG. 9B). Four weeks after the transplantation, absorption of implants and neonatal bones was observed (FIGS. 10A to 10C). It was observed that absorption of implants and neonatal bones was further enhanced 6 weeks after the transplantation (FIGS. 11A to 11C).

(3) HAp/Col Porous Body Surface-crosslinked with 0.05% GA

This porous body had frequent crosslinking. Thus, absorption of implants was poor, and implants still remained even 6 weeks after the transplantation (FIG. 12D).

All publications, patents, and patent applications cited herein are incorporated herein by reference in their entirety.

INDUSTRIAL APPLICABILITY

The present invention enables the production of biodegradable porous and composite materials which have large pore diameters, high porosities, and mechanical strengths that are suitable for alternative bone implants. The porous and composite materials produced by the present invention are very useful as implants, various carriers such as drug carriers for sustained-release, and supports for cell culture.

The invention claimed is:

1. A process for producing porous and composite materials comprising steps of: cooling a complex containing at least one calcium salt selected from calcium carbonate, calcium phosphate, and hydroxyapatite and collagen, at least a part of which is gelatinized, to gelate the gelatin; freezing it; and then lyophilizing the resultant.

2. A process for producing porous and composite materials comprising a step of introducing surface crosslinking between collagens to the porous and composite materials obtained by the process according to claim 1.

3. The process according to claim 2, wherein the step of introducing surface crosslinking is carried out by immersing the porous and composite materials in a solution containing a crosslinking agent.

4. The process according to any one of claims 1 to 3 comprising a step of adding a crosslinking agent to gelatinized collagen to introduce internal crosslinking between collagens.

5. The process according to any one of claims 1 to 3, wherein the calcium salt is hydroxyapatite.

6. A process for producing porous and composite materials comprising the following steps of:
   1) gelatinizing at least a part of the collagen constituting a complex containing hydroxyapatite and collagen;
   2) introducing internal crosslinking between collagens with the addition of a crosslinking agent to the complex;
   3) obtaining porous and composite materials by cooling the complex to gelate the gelatin, freezing it, and then lyophilizing the resultant; and
   4) introducing surface crosslinking between collagens by immersing the porous and composite materials in a solution containing a crosslinking agent.

7. The process according to claim 2 or 3, wherein internal and/or surface crosslinking between collagens is introduced using glutaraldehyde as a crosslinking agent.

8. The process according to any one of claims 1 to 3, wherein surface crosslinking between collagens is introduced by immersing the porous and composite materials in a solution containing a crosslinking agent comprising ethanol as a solvent.

9. The process according to any one of claims 1 to 3, wherein the resulting porous and composite materials have porosities of 80% or higher.

10. The process according to any one of claims 1 to 3 using a complex comprising the c-axis of hydroxyapatite being oriented along collagen fibers.

11. Porous and composite materials having porosities of 80% or higher, which are produced by the method according to any one of claims 1 to 3.

12. Implants of the porous and composite materials according to claim 11.

* * * * *